United States Patent
Shibata et al.

(10) Patent No.: US 7,440,092 B2
(45) Date of Patent: Oct. 21, 2008

(54) METHOD AND APPARATUS FOR DETECTING DEFECTS

(75) Inventors: Yukihiro Shibata, Fujisawa (JP); Shunji Maeda, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/602,247

(22) Filed: Nov. 21, 2006

(65) Prior Publication Data
US 2007/0064225 A1 Mar. 22, 2007

Related U.S. Application Data

(63) Continuation of application No. 10/020,977, filed on Dec. 19, 2001, now Pat. No. 7,142,294.

(30) Foreign Application Priority Data
Dec. 20, 2000 (JP) ............... 2000-391825

(51) Int. Cl.
G01N 21/00 (2006.01)
G06K 9/00 (2006.01)
(52) U.S. Cl. ............. 356/237.2; 356/237.3; 356/237.4; 382/149
(58) Field of Classification Search ............... None
See application file for complete search history.

(56) References Cited

U.S. PATENT DOCUMENTS

| | | | |
|---|---|---|---|
| 4,860,371 A * | 8/1989 | Matsuyama et al. ......... 382/149 |
| 5,479,252 A | 12/1995 | Worster | |
| 5,774,222 A | 6/1998 | Maeda | |
| 5,864,394 A * | 1/1999 | Jordan et al. ............. 356/237.2 |
| 6,034,776 A * | 3/2000 | Germer et al. ............. 356/369 |
| 6,169,282 B1 * | 1/2001 | Maeda et al. ............. 250/310 |
| 6,288,780 B1 | 9/2001 | Fairley | |
| 6,373,565 B1 * | 4/2002 | Kafka et al. ............. 356/237.4 |
| 6,535,621 B1 | 3/2003 | Fujita | |
| 6,621,568 B1 | 9/2003 | Yonezawa | |
| 6,621,570 B1 | 9/2003 | Danko | |
| 6,621,571 B1 | 9/2003 | Maeda | |

(Continued)

FOREIGN PATENT DOCUMENTS

JP 08-327554 12/1996

(Continued)

Primary Examiner—Gregory J Toatley, Jr.
Assistant Examiner—Gordon J Stock, Jr.
(74) Attorney, Agent, or Firm—Antonelli, Terry, Stout & Kraus, LLP.

(57) ABSTRACT

A method and apparatus for detecting a defect in which image signals of a same area of a sample are obtained by imaging the sample under different optical conditions, and the obtained image signals are analyzed and optical conditions are selected which modify a contrast in the image signal. Image signals of the sample under the selected optical conditions are obtained by imaging the sample with an inspection system, and the images under the selected optical conditions are evaluated to adjust optical conditions for inspection including an inspection threshold, which is greater than a maximum contrast difference among false defects detected at the step of obtaining and with which a maximum number of actual defects can be detected. A defect of the sample is detected by processing the image signals of the sample obtained through the inspection system under the adjusted optical conditions.

6 Claims, 8 Drawing Sheets

U.S. PATENT DOCUMENTS

| | | |
|---|---|---|
| 6,937,753 B1 * | 8/2005 | O'Dell et al. ............... 382/141 |
| 6,947,587 B1 | 9/2005 | Maeda |
| 7,142,294 B2 * | 11/2006 | Shibata et al. ........... 356/237.2 |

FOREIGN PATENT DOCUMENTS

| | | |
|---|---|---|
| JP | 10160681 A * | 6/1998 |
| JP | 2000-105203 | 4/2000 |
| JP | 2000-155099 | 6/2000 |

\* cited by examiner

| TRANSMISSION RATIO OF 0-TH ORDER DIFFRACTED LIGHT | DIFFERENTIAL VALUE OF IMAGE |
|---|---|
| 100% | 288,126 |
| 80% | 312,390 |
| 60% | 226,985 |
| 40% | 479,925 |
| 20% | 287,175 |

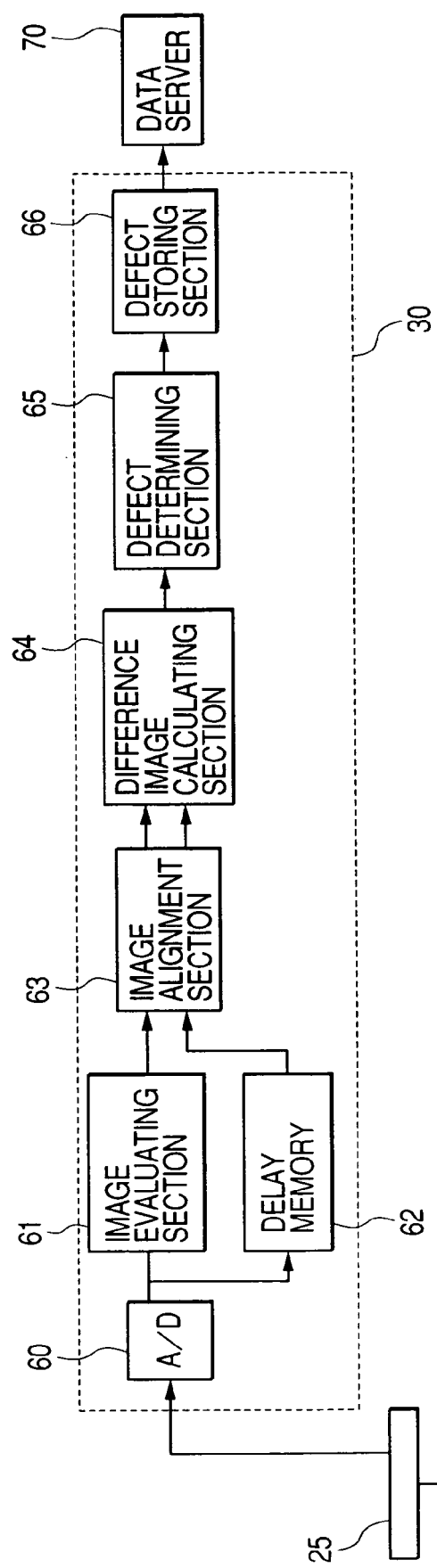
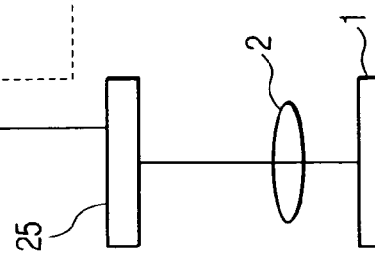

FIG. 11

| EVALUATION VALUE | DESCRIPTION |
|---|---|
| DIFFERENTIAL VALUE | PERFORM SECONDARY DIFFERENTIATION OF AN IMAGE AND SUM UP THE SECONDARY DIFFERENTIAL VALUES.<br>EXAMPLE OF THE DIFFERENTIAL VALUE:<br>  CALCULATE CONTRAST DIFFERENCE VALUES BETWEEN THE PIXEL TO BE DIFFERENTIATED AND ADJACENT EIGHT PIXELS RESPECTIVERY,<br>  CALCULATE SUMMATION OF ABSOLUTE VALUES OF THESE VALUES AS THE DIFFERENTIAL OF THE IMAGE, AND THEN CALCULATE THE DIFFERENTIAL FOR EACH PIXEL OF THE IMAGE |
| MAXIMUM CONTRAST DIFFERENCE IN DIVIDED REGIONS | DIVIDE AN IMAGE INTO REGIONS OF A PREDETERMINED SIZE, ACQUIRE THE MINIMUM AND MAXIMUM CONTRAST VALUES FOR EACH DIVIDED REGION, AND THEN CALCULATE THE DIFFERENCE OF THE MINIMUM AND MAXIMUM VALUES AS THE MAXIMUM CONTRAST DIFFERENCE. THEN CALCULATE THE MAXIMUM CONTRAST DIFFERENCE VALUES FOR ALL DIVIDED REGIONS AND SUM UP ABSOLUTE VALUES OF THE MAXIMUM CONTRAST DIFFERENCE VALUES.<br>EXAMPLE OF DIVISION: A REGION OF 3×3 PIXELS IN AN IMAGE IS DEFINED AS ONE SEGMENT. |
| CONTRAST DISPERSION VALUE | DIVIDE AN IMAGE INTO REGIONS OF A PREDETERMINED SIZE, AND ACQUIRE DISPERSION OF A CONTRAST VALUE FOR THE DIVIDED REGION. ACQUIRE THE DISPERSION VALUE FOR ALL DIVIDED REGIONS AND SUM UP THE VALUES.<br>EXAMPLE OF DIVISION: A REGION OF 3×3 PIXELS IN AN IMAGE IS DEFINED AS ONE SEGMENT. |
| IMAGE FOURIER TRANSFORMATION DENSITY | PERFORM TWO-DIMENSIONAL FOURIER TRANSFORMATION IN X AND Y DIRECTIONS OF AN IMAGE AND SUM UP SPECTRAL DENSITY VALUES OF FREQUENCY NOT LESS THAN A PREDETERMINED FREQUENCY VALUE. |

METHOD AND APPARATUS FOR DETECTING DEFECTS

CROSS REFERENCE TO RELATED APPLICATION

This application is a continuation of U.S. application Ser. No. 10/020,977, filed Dec. 19, 2001, now U.S. Pat. No. 7,142,294, the contents of which are incorporated herein by reference.

BACKGROUND OF THE INVENTION

The present invention relates to a high resolution optical system for inspection and observation of fine pattern defects, foreign particles and the like that is typically performed in manufacturing process of semiconductors and flat panel displays and also relates to a method and an apparatus for detecting defects by using such optical system.

As a prior art, Japanese Patent Laid-open No. Hei 8-327554 discloses a technique for improving contrast of an object by changing an impinging angle of illumination depending on optical characteristics of the object to be observed.

In the above prior art, the impinging (incident) angle of the illumination is changed and determined so that minute unevenness on a surface of the object becomes obvious by improving the contrast of the unevenness. In such method, an optical system for oblique illumination and oblique detection is utilized, wherein the optical system changes a viewing mode of the object from bright field illumination to dark field illumination continuously by changing the impinging angle of the oblique illumination. However, for example, in the dark field illumination mode, it may be difficult to detect certain defects such as residual thin films, if any. Further, when semiconductor devices are inspected, minute unevenness (grains) may be appeared on a surface of metal wiring created in a metallization process. Such grains are not fatal for the semiconductor devices and therefore should not be detected as defects, however in the above prior art, it has been difficult to distinguish such grains from other defects properly to perform more reliable defect detection.

SUMMARY OF THE INVENTION

According to an object of the present invention, it is possible to implement more reliable defect detection that has been difficult to accomplish in the above prior art.

In particular, a method of the present invention comprises the steps of: obtaining an image signal of a sample by picking up (imaging) the sample through an optical system; adjusting optical conditions of the optical system so as to decrease a difference of contrast or contrast of a pattern in the image signal among segments (points) corresponding to a plurality of regions (positions) on the sample; obtaining the image signal of the sample under the adjusted optical conditions by picking up (imaging) the sample through the optical system having the adjusted optical conditions; and detecting a defect of the sample by processing the image signal.

Also, a method of the present invention comprises the steps of: obtaining an image signal of a sample by illuminating and picking up (imaging) the sample; adjusting a transmission (detection) ratio of 0-th order diffracted light (regular reflected light) included in reflected light reflected from the sample in according with illumination so as to decrease a difference of contrast or contrast of a pattern in the image signal among segments (points) corresponding to a plurality of regions (positions) of the sample; obtaining the image signal of said sample with the adjusted transmission ratio of the 0-th order diffracted light by picking up the sample under the conditions in that the transmission ratio of the 0-th order diffracted light has been adjusted; and detecting a defect of the sample by processing the image signal.

Further, a method of the present invention comprises the steps of: illuminating a sample; obtaining a plurality of images having different transmission ratios of 0-th order diffracted light included in entire light generated by the illumination and reflected from the sample by changing the transmission ratio of the 0-th order diffracted light and imaging the sample; determining conditions for the transmission ratio of the 0-th order diffracted light on which defect detection sensitivity is increased by using the plurality of images; setting the transmission ratio of the 0-th order diffracted light included in the entire light reflected from the sample to the determined conditions for the transmission ratio; obtaining the image by imaging the sample under the determined conditions for the transmission ratio; and detecting a defect of the sample by using the image captured under the determined conditions for the transmission ratio.

Still further, a method of the present invention comprises the steps of: illuminating a sample with polarized light; obtaining an image of the sample by imaging the illuminated sample; adjusting polarization conditions of light generated by the illumination and reflected from the sample based upon contrast information about the image of the sample; obtaining the image of the sample by imaging the sample under the adjusted polarization conditions of the reflected light; and detecting a defect of the sample by using the image.

According to the present invention, it is possible to obtain a high resolution image. Further, it is also possible to set optical conditioning automatically in a short time.

These and other objects, features and advantages of the invention will be apparent from the following more particular description of preferred embodiments of the invention, as illustrated in the accompanying drawings.

BRIEF DESCRIPTION OF THE DRAWINGS

FIG. 9 is a block diagram showing a general configuration of an image processing section according to the present invention;

FIG. 10 is a diagram showing an operation of secondary differential; and

FIG. 11 is a table showing an example of a relationship between evaluation values and descriptions of these values.

DESCRIPTION OF THE PREFERRED EMBODIMENTS

Figure 5:
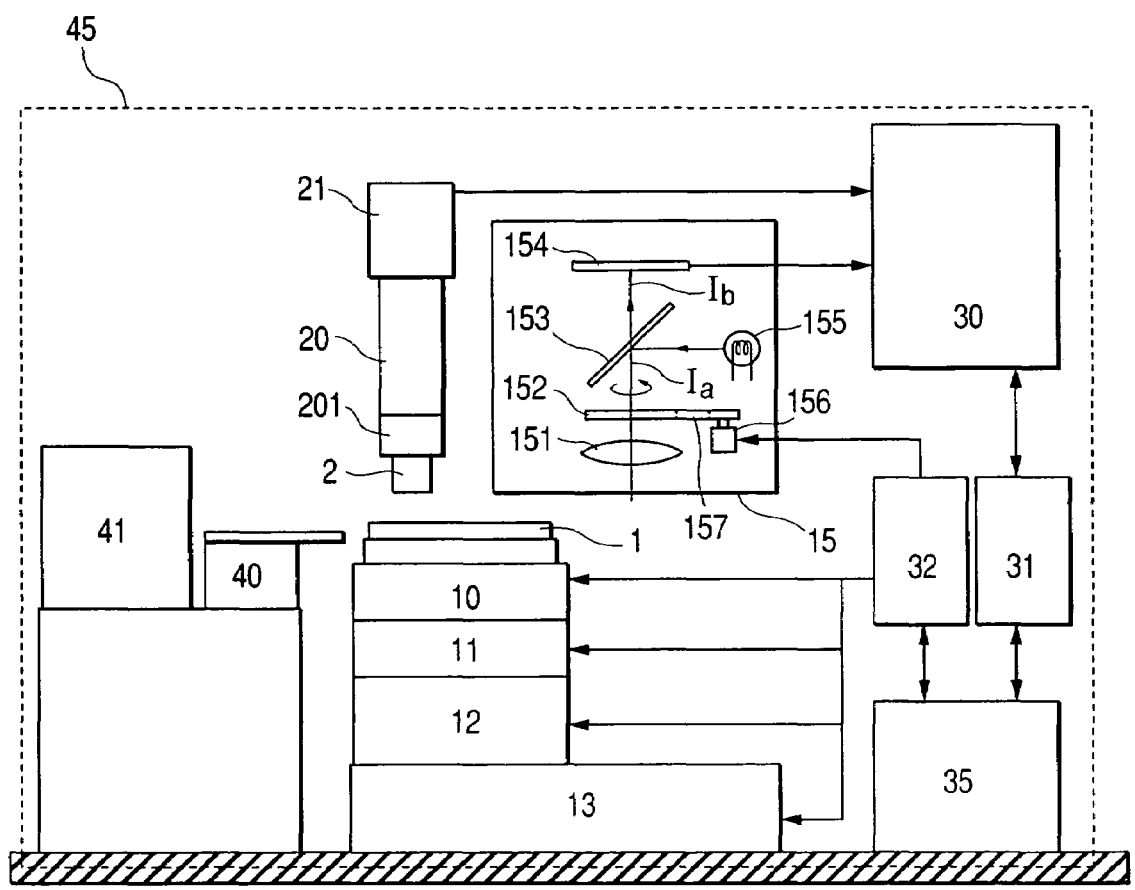
FIG. 5 is a front view showing a general configuration of an inspection apparatus according to the present invention.

An embodiment of the present invention is shown in FIG. 5. A sample (a wafer) 1 contained in a cassette 41 is transported to a Z-stage 10, a θ-stage 11, an X-stage 12 and a Y-stage 13 by a wafer transporting robot 40 of a system 45. The wafer 1 that has been transported to any one of the stages is moved into a field of view of a sub-optical system 20 having low magnification for detection in an entire chip area to detect an image of the entire chip area. Then, the chip image being divided into a peripheral circuit 2a1, a logic part 2a2, a memory part 2a3 and the like, is captured by a camera 21 in the sub-optical system 20. This image is transferred to an image processing section 30. This image is stored in a data server 31. The system is configured so that this image may be shown on a display of an operating computer 35 in this inspection apparatus. Therefore, the operating computer 35 can select a region (a peripheral circuit part 2a1, a logic part 2a2, a memory part 2a3 and the like) to acquire an image for conditioning the transmission ratio (Ib/Ia) of the 0-th order diffracted light, on the display. The sub-optical system 20 for detection in an entire chip area is provided a polarizing conditions adjusting section 201 which comprises a PBS and a half wave plate or a quarter wave plate, and an objective lens 2.

However, in an actual inspection, an image is detected while a surface of the wafer 1 is scanned in a field of view of an optical system 15 for visual inspection. Then, this image data detected by the image sensor 154 also transfers to the image processing section 30, and then candidate defects are sought by comparatively checking with images of adjacent chips. An inspection result is stored in the data server 31 and read when the result is reviewed. It is noted that mechanical operating sections such as the stages and the like (a drive motor 156) are controlled by a mechanical controller 32.

The optical system 15 using in the actual inspection is formed by coaxial bright field epi-illumination system. Then, the optical system 15 is provided with an objective lens 151, a half wave plate or a quarter wave plate 152, a drive motor 156 for adjusting minute rotation of the wave plate 152, a belt 157 for transferring an rotation output of the drive motor to the minute rotation of the wave plate 152, a PBS (polarizing beam splitter) 153, an image sensor 154 for imaging each region and a light source 155. The light source 155 is formed by a laser source such as a semiconductor laser, an argon laser, a YAG-SHG laser or an exima laser, or a discharge tube such as a xenon lamp, or a mercury lamp, or a filament light source such as a halogen lamp. The image sensor 154 is formed by a TDI image sensor or a CCD image sensor. The PBS 153 converts by reflecting a light outputted from the light source 155 to a linear polarized light. Further, the wave plate 152 converts the linear polarized light to an elliptically polarized light. Therefore, the elliptically polarized light is irradiated by focusing through the objective lens 151 on the region of the wafer 1.

The high order diffracted light be generated from the edge of pattern of the region is condensed by the objective lens 151 and is converted to the ellipse polarized light by the wave plate 152. On the result, the high order diffracted light is transmitted through the PBS 153 and is detected as image by the image sensor 154. On the other hand, the 0-th order diffracted light (regular reflected light) be generated from the pattern of the region is condensed by the objective lens 151 and is converted to the linear polarized light by the wave plate 152. The PBS 153 splits the 0-th order diffracted light into the transmission light and the reflection light. Therefore, the transmission ratio (Ib/Ia) of the 0-th order diffracted light through the PBS 153 can adjust by varying the elliptically polarized condition in accordance with controlling the minute rotation angle of the wave plate 152.

Ib is an intensity of the 0-th order diffracted light transmitted through the PBS 153.

Ia is an intensity of the 0-th order diffracted light inputted to the PBS 153.

On case of the other embodiment, the wave plate is removed and a half mirror is provided instead of the PBS 153. Further, a spatial filter (not shown) is provided on a Fourier transform plane of the surface of the wafer 1 or in the neighborhood of the Fourier transform plane in the optical system 15. The spatial filter shields the 0-th order diffracted light and transmits the high-order (not less than 1-th order) diffracted light. So, a plurality of spatial filters in which each of shielding portions has different size, are prepared. The adjustment of the transmission ratio (Ib/Ia) of the 0-th order diffracted light can perform by changing some spatial filter into different spatial filter.

According to above mention, the minute rotation adjustment of the wave plate 152 or the change of the spatial filters can adjust the transmission ratio (Ib/Ia) of the 0-th order diffracted light (an optical condition of the optical system 15) so as to decrease a difference of contrasts (amplitude M of intensity) or contrasts of a pattern in the image signals detected by the image sensor 154 (25) among points (segments) corresponding to a plurality of regions (a peripheral circuit part 2a1, a logic part 2a2, a memory part 2a3 and the like in a chip) of the wafer 1.

The optical system 15 comprises a polarizing conditions adjusting section 152, 153 for adjusting polarizing conditions of both illuminating light for the wafer 1 and reflecting light from the wafer 1, which acts as elements for adjusting contrast M (amplitude of intensity) of the detected image.

Figure 1:
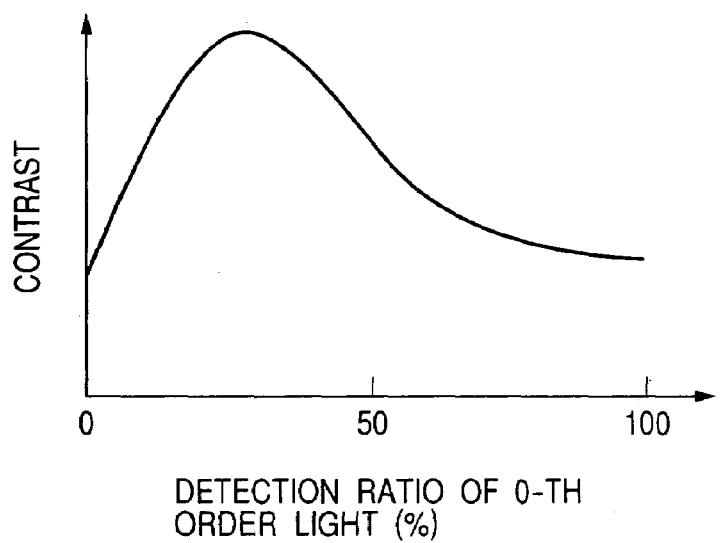
FIG. 1 is a graph showing a relationship between a transmission ratio of 0-th order diffracted light and contrast of an image.

FIG. 1 shows a relationship between the transmission ratio (Ib/Ia) of 0-th order diffracted light and pattern contrast of a detected image. When the transmission (detection) ratio of the 0-th order light is 100%, the image is the same as the one that is detected in a typical bright field detection manner. As the transmission ratio of the 0-th order light decreases by adjusting polarizing conditions using the polarizing conditions adjusting section 152, 153, amplitude of higher order diffracted light approaches amplitude of the 0-th order diffracted light, which initially results in improved contrast. However, as the transmission ratio of the 0-th order diffracted light further decreases, contrast will be reduced. It is because the amplitude of the higher order diffracted light becomes too high, and as a result of which the contrast (modulation) generated by interference between the 0-th order light and the higher order diffracted light decreases.

Figure 2:
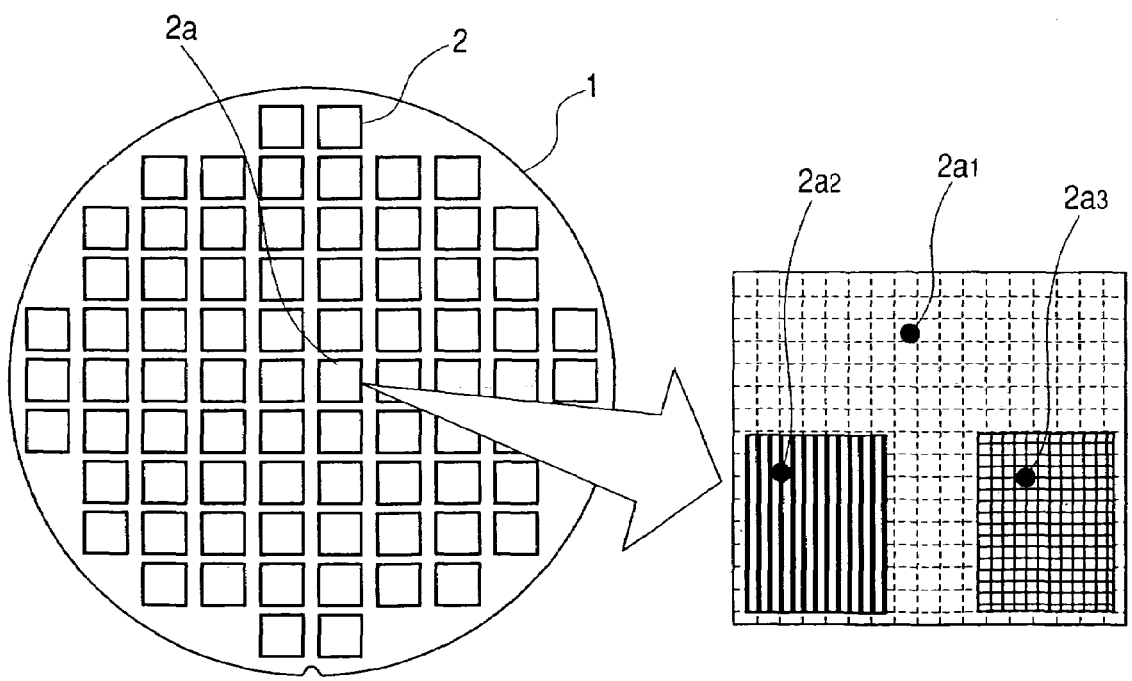
FIG. 2 is a top plan view showing appearance of a wafer for memory merged logic products.

FIG. 2 shows appearance of a wafer to be inspected. On the wafer 1, a similar pattern is formed in every die (chip) 2. For example, in semiconductor products in which memory and logic circuits are combined, each die region of a representative chip 2a of the chips 2, as shown, is divided into a peripheral circuit part 2a1, a logic part 2a2, a memory part 2a3 and the like. A width and a density of the pattern formed in each region usually varies. Here, assume the pattern width and pattern density of each region (part) as follows: (i) the peripheral circuit part 2a1 has a large pattern width and a low pattern density; (ii) the logic part 2a2 has a fine pattern width but a relatively low pattern density; and (iii) the memory part 2a3 has a fine pattern width and a high pattern density.

Figure 3:
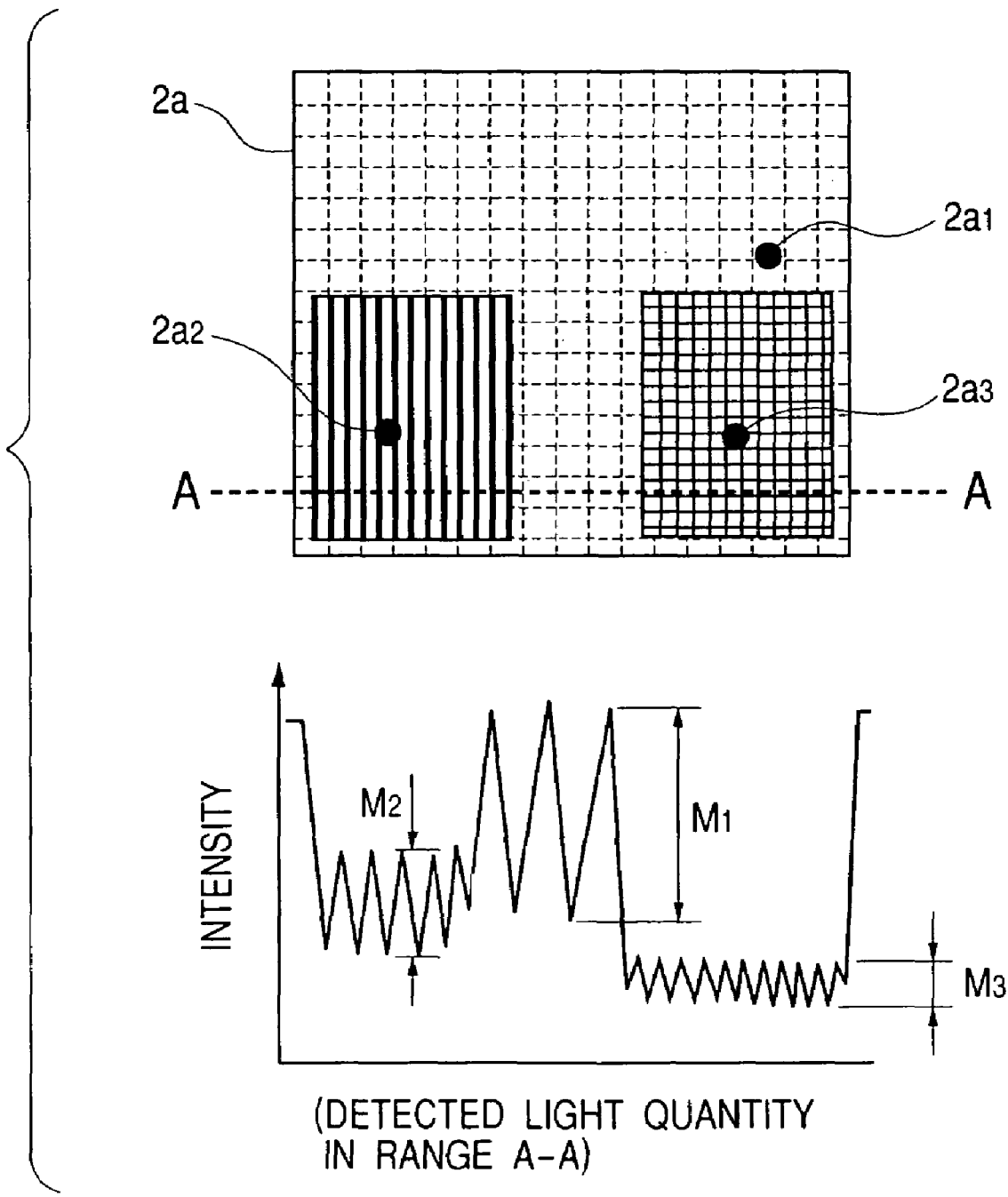
FIG. 3 is a top plan view with a distribution diagram of light quantity showing an example of a detected image by conventional bright field illumination.

FIG. 3 shows an example of an image obtained from the die region of the representative chip 2a by conventional bright field detection. Considering distribution of detected light quantity (intensity) in a range A-A of the detected image, it can be found that the peripheral circuit part 2a1 having the large pattern width and the low density shows high pattern modulation M1. The memory part 2a3 having the fine pattern width and the high density is generally detected darkly and has low modulation M3. In addition, M2 shows modulation in the logic part 2a2. Such generally dark detection of the memory part 2a3 results from reduction of ratios of the 0-th order light and the higher order diffracted light captured by an objective lens. In a defect inspection, a difference between images of adjacent dies is firstly acquired by difference image calculating section 64, and then points having values beyond a threshold are determined as defects by defect determining section 65. Therefore, inspection sensitivity is reduced in a region (part) having low modulation of the detected image. Thus, in order to have uniform defect detection sensitivity, it is desirable that the modulation (contrast) is equal in the entire die region irrespective of the pattern width and the pattern density.

Figure 4:
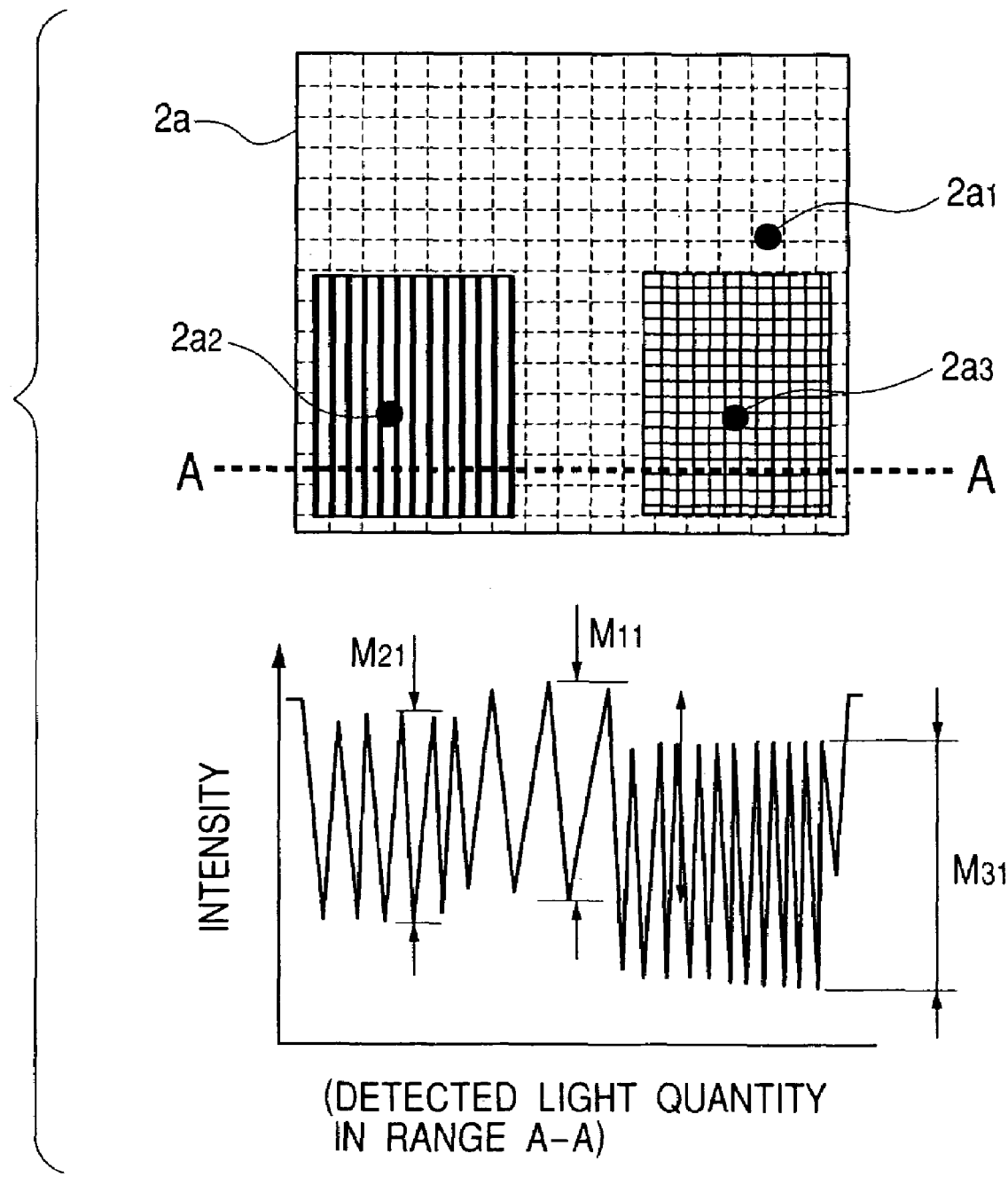
FIG. 4 is a top plan view with a distribution diagram of light quantity showing an example of a detected image when a transmission ratio of 0-th order diffracted light is reduced.

FIG. 4 shows a detected image of the representative chip 2a when the transmission ratio of the 0-th order light is set to approximately 40%. Considering the fact that the low contrast (modulation) in the memory part 2a3 results from a reduced converging ratio of the higher order diffracted light by the objective lens 151 (2), it is possible to detect the amplitude of the 0-th order light and the higher order diffracted light equally and to improve the modulation M31 due to interference by reducing the 0-th order light. Further, with the reduced 0-th order diffracted light, the modulation M11 of peripheral circuit part 2a1 having a large pattern width shows a lower intensity (brightness) level as compared to the one before the reduction of the 0-th order light. In addition, M21 shows modulation in the logic part 2a2. Thus, it is possible to improve the contrast in regions having a fine pattern width by reducing the 0-th order light, though at this time it is necessary to increase an illumination light quantity as the detection ratio of the light quantity decreases as a result of the reduced 0-th order light. Accordingly, the inspection sensitivity in the parts having a fine pattern can be improved.

Further, when a wafer having embedded memory is inspected, the memory part is inspected by cell-by-cell comparison, while the other parts are inspected by die-by-die comparison. These inspection procedures may be either performed in two steps separately, or performed simultaneously in a combined inspection method. In view of inspection performance, the combined inspection method may be advantageous because it can be performed in a short time. Still further, the modulation in the cell part due to reduction of the 0-th order light is increased, whereby also the inspection sensitivity can be improved.

Figure 6:
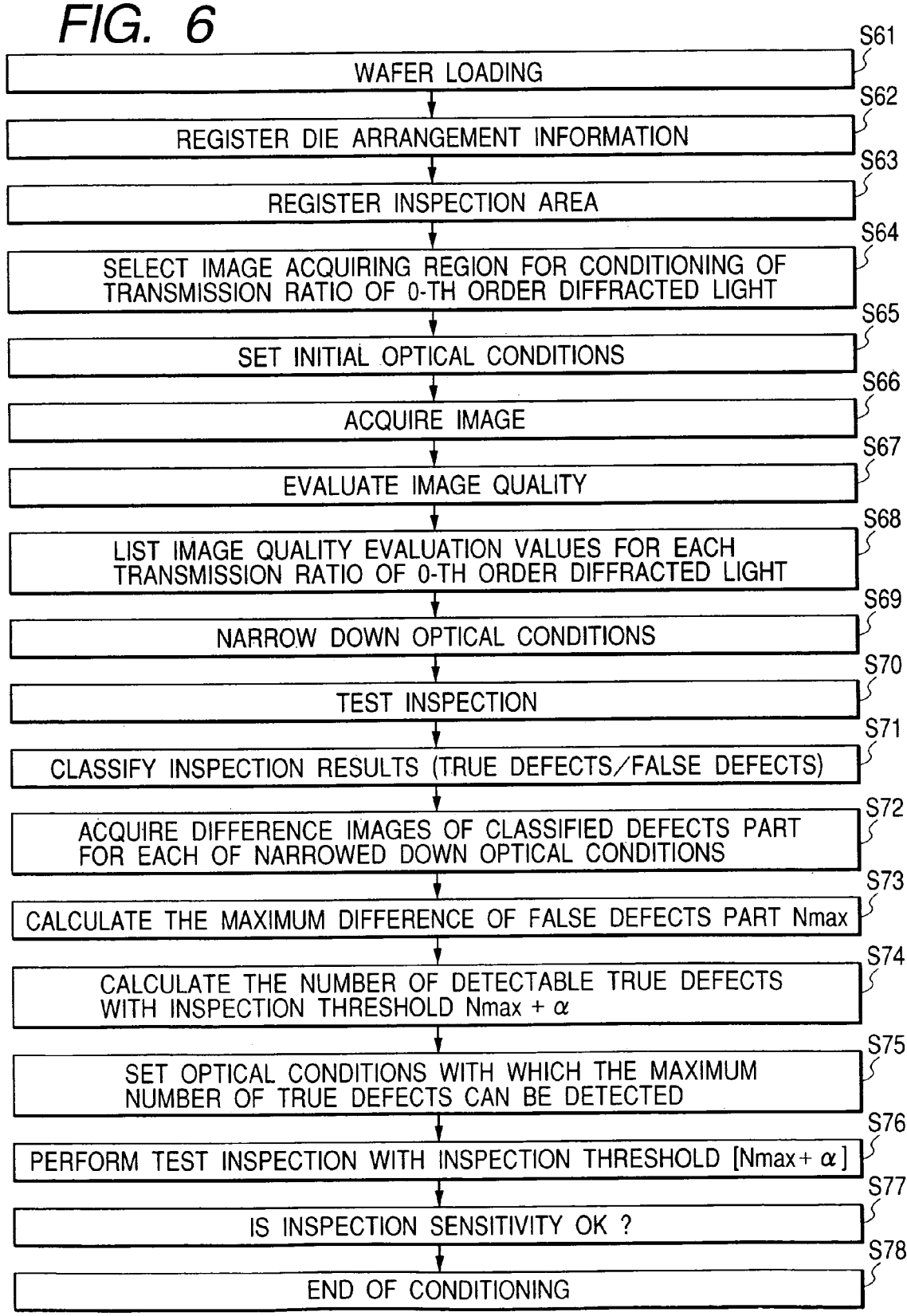
FIG. 6 is a flow chart showing a procedure for conditioning the detection ratio of the 0-th order diffracted light.

Since every wafer to be inspected varies in a pattern width and a pattern density, it is necessary to condition the detection ratio of the 0-th order diffracted light (regular reflected light) for the defect inspection in advance. FIG. 6 shows a flowchart of such inspection. A wafer to be inspected is loaded on the stage 10-13 into an inspection apparatus (S61). Then information about a die arrangement in the wafer is registered to the operating computer 35 or the data server 31 (S62). Then, coordinates of an inspection area in a die are registered to the operating computer 35 or the data server 31 (S63). Then, a region to acquire an image for conditioning the transmission (detection) ratio of the 0-th order diffracted light is selected on the display of the operating computer 35 (S64).

Initial optical conditions are set for half wave ($\frac{1}{2}\lambda$) plate or quarter wave ($\frac{1}{4}\lambda$) plate 152 in the optical system 15 through the mechanical controller 32 by the operating computer 35 (S65). Then the image of the conditioning region is acquired while a surface of the wafer 1 is scanned in a field of view of an optical system 15 for visual inspection (S66). Then, contrast (modulation) of the acquired image is evaluated by the image processing section 30 (S67). Then, images with varying transmission ratio of the 0-th order diffracted light by controlling the rotation of half wave plate or quarter wave plate 152 are acquired by the optical system 15 and evaluated by the image processing section 30. After the evaluation of the images has been completed, image evaluation values determined for each transmission ratio of the 0-th order diffracted light are listed on a display (S68).

The series of varying transmission ratios of the 0-th order diffracted light is narrowed down to a plurality of transmission ratios having relatively higher evaluation values (S69). Then, a test inspection is performed with sensitivity including false defects by using the optical system 15 (S70). And defects to be detected are classified as true or false defects by the image processing section 30 (S71). Images of the true and false defects parts are detected for each of the plurality of narrowed-down detection ratios of the 0-th order diffracted light by the optical system 15 and difference images for each detection ratio are computed by the image processing section 30 (S72). Then, the maximum contrast difference of the false defects part Nmax is determined for each transmission ratio of the 0-th order diffracted light by the image processing section 30 (S73). Further, for each transmission ratio of the 0-th order light, when an inspection threshold is determined by adding a constant $\alpha$ to the Nmax, the number of the detectable true defects is calculated by the image processing section 30 (S74). The transmission ratio of the 0-th order diffracted light with which the maximum number of the true defects can be detected is set as a condition of the actual inspection for the region selected by step S64 (S75). Then, setting the inspection threshold to [Nmax +$\alpha$], the test inspection is performed for the particular region (S76), and then, if desirable sensitivity is satisfied (S77), the conditioning procedure is completed (S78). Hereinafter, the actual inspection will be performed with the conditioned sensitivity under the conditions in that the transmission ratio of the 0-th order diffracted light has been adjusted for each of a peripheral circuit part 2a1, a logic part 2a2, a memory part 2a3 and the like in a die (chip).

Figures 7, 8:
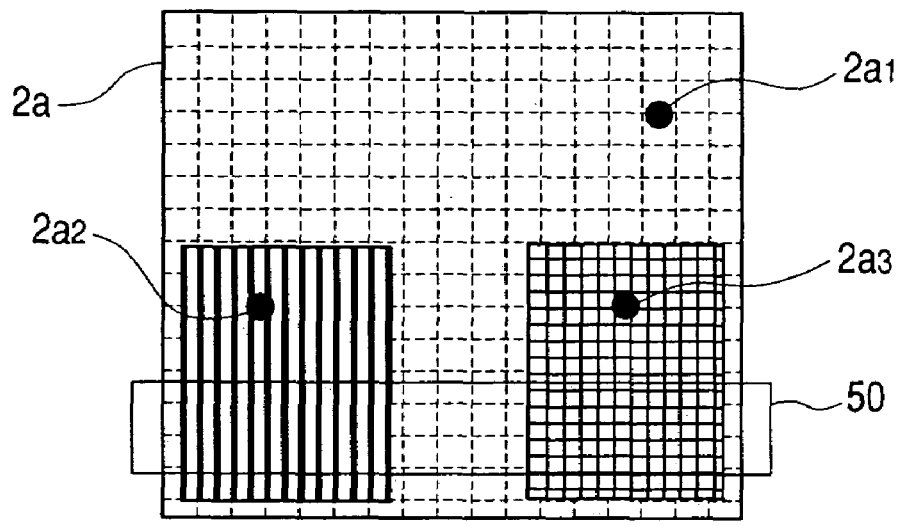
FIG. 7 is a top plan view showing an example of a region for obtaining an image for conditioning.
FIG. 8 is a table showing an example of an image evaluation result.

FIG. 7 shows a schematic diagram of an image region 50 that is acquired for conditioning the transmission ratio of the 0-th order diffracted light. If the pattern width and the pattern density in the die can be divided into a plurality of segments, it is desirable that each of the segments includes regions that correspond to every pattern width and pattern density that may be observed in the die. However, if there is no preliminary information used for the segmentation, it may be contemplated to set a central field of the die as a default segment, and the like. Alternatively, the image that has been acquired by the optical system for detection in an entire chip area 20 may be used to determine the image-acquiring region.

FIG. 8 shows an example of summed differential values of the images acquired for each transmission (detection) ratio of the 0-th order diffracted light. In this calculation result, it is noted that about 40% of the transmission ratio of the 0-th order diffracted light shows the highest summed differential value and therefore such transmission ratio is advantageous for a defect inspection. Considering these summed differential values, various conditions for the transmission ratio of the 0-th order light listed in FIG. 8 are narrowed down to two conditions, i.e. 40% and 60%, and then the image of the true and false defects parts shown in FIG. 6 is acquired to determine the conditions of the transmission ratio of the 0-th order light for the actual inspection.

FIG. 9 shows a block diagram of the image processing section 30. An image of a wafer 1 is magnified and projected on an image sensor 25 (154) by an objective lens 2 (151). An output signal of the image sensor 25 (154) is converted into a digital signal in an A/D converting section 60. The detection digital signal is, on one hand, sent to an image evaluating section 61 for evaluation of image quality. On the other hand, the detection digital signal is stored in a delay memory 62 temporarily and is formed as a reference digital signal for comparing between images of adjacent chips or cells. Each of the detection digital signal and the reference digital signal is performed relative alignment of the images in an image alignment section 63. Then, a difference image between the detection digital signal and the reference digital signal is calculated in a difference image calculating section 64, and then a feature amount of the difference is sent to a defect determining section 65. In the defect determining section 65, coordinates of the feature amount that exceeds the inspection threshold is determined. The position of such coordinates is considered as a candidate defect, and the coordinates, feature amount and so on are stored in the defect storing section 66. Data in the defect storing section 66 is sent to a data server 70 and stored in a hard disk.

FIG. 10 shows an operation of secondary differential that is one of evaluation values for conditioning the transmission ratio of the 0-th order diffracted light in the step S67 of evaluating the image quality as shown in FIG. 6. By way of example, assume that a light quantity of a pixel for which the secondary differential is to be calculated is I (x, y). Difference values between I (x, y) and adjacent eight pixels are calculated respectively, and summation of absolute values of these eight difference values is considered as the secondary differential of I (x, y). The evaluation value is acquired by performing the above operation for each pixel of the detected image and summing the secondary differential values for each of pixels.

FIG. 11 shows a list of evaluation values to narrow down the transmission ratio of the 0-th order diffracted light in the step S66 of listing the image quality evaluation values for each transmission ratio of 0-th order diffracted light as shown in FIG. 6. A differential value is acquired by performing secondary differentiation of detected images for each transmission ratio of the 0-th order diffracted light and then summing the secondary differential values. This operation is performed as described in FIG. 10.

Next, the maximum contrast difference in divided regions is described. A detected image is divided into regions of a predetermined size, the minimum and the maximum contrast value are acquired for each divided region, and then the difference between the minimum and the maximum values is calculated as the maximum contrast difference. The maximum contrast difference values are calculated for all divided regions and absolute values of the maximum contrast difference values are summed. As an example of how to divide a detected image into regions, a region of 3 pixels x 3 pixels in X, Y coordinates of the image may be defined as one segment. Since the one segment contains brightness information for 9 pixels, a contrast difference value for the one segment can be acquired by determining a difference between the maximum and the minimum value for such 9 pixels. Considering the fact that the contrast difference value for the one segment corresponds to contrast of the pattern image of such segment, the larger the maximum contrast difference value is, the more advantageous the value is for defect inspection. Therefore, since the larger summation value of the maximum contrast difference values is also more advantageous for defect inspection, it is contemplated to select the inspection conditions for the transmission ratios of the 0-th order diffracted light that have the larger summation value as candidate conditions for actual inspection. Here, it is to be noted that the maximum contrast difference value indicated here does not include variations other than wafer pattern information, such as a sampling error of an image, variations of partial illumination distribution and the like.

Next, a contrast dispersion value is described. An image is divided into regions of a predetermined size, and dispersion of a contrast value is acquired for the divided region. The dispersion value is acquired for all divided regions and the values for all divided regions are summed. As an example of division into regions, 3×3 pixels may be set to one segment. Here, it is to be noted that this dispersion value indicates variations of contrast in the divided regions, and therefore, the higher the dispersion value is, the more the pattern information should be. Thus, a higher dispersion value is more advantageous for defect inspection. Here, it is to be noted that the contrast variations indicated here does not include variations other than wafer pattern information, such as a sampling error of an image, variations of partial illumination distribution and the like.

Next, an evaluation method by image Fourier transformation density is described. Two-dimensional Fourier transformation is performed in X and Y directions of an image and then summation of a spectral density value of frequency not less than a predetermined frequency value is defined as an evaluation value. The predetermined frequency value is determined with reference to a pattern pitch, pixel dimensions of the image sensor 154 (25) that are converted into actual dimensions on a wafer 1 and the like. The high spectral density of frequency not less than the predetermined frequency value means high contrast (modulation) of the image in the fine pattern not larger than the pattern pitch dimensions that correspond to the predetermined frequency. Thus, higher spectral density is more advantageous for defect inspection. Further, it is also possible to use spectral density for the predetermined frequency only as an evaluation value.

Though the embodiment wherein the polarizing conditions adjusting section 152, 153 is used as contrast adjusting means is described in the above description, similar effects may be obtained by using a spatial filter. In this case, in order to change the transmission ratio of the 0-th order diffracted light, a plurality of the spatial filters that correspond to various transmission ratios may be used selectively, or the spatial filter may have variable construction so as to form a suitable pattern that corresponds to various transmission ratios.

In the above description, a plurality of evaluation values are described, in an actual inspection, a single or more than one evaluation value(s) may be used to narrow down the reduction ratios of the 0-th order diffracted light.

Further, it is noted that the following optical parameters other than the reduction ratio of the 0-th order light may be used for contrast adjustment:

(i) illumination σ (setting of an incidence angle range of illumination);

(ii) a wavelength range of illumination; and (iii) the number of apertures NA of the objective lens 151 (2).

The evaluation values of the present invention may be also utilized effectively to narrow down these conditions. By using the evaluation values of the present invention, it is possible to set optical conditions that are advantageous in view of inspection sensitivity in a short time.

As described above, in accordance with the present invention, defect detection sensitivity in the fine pattern part can be improved by improving the contrast of image in the fine pattern part. Each parameter for optical conditions to improve the contrast of image in the fine pattern part can be set in a shorter time, and therefore the amount of time to prepare an inspection recipe can be reduced substantially.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An inspection method, comprising the steps of:
    illuminating a polarized light onto a specimen which has plural chips in which patterns are formed in each chip;
    detecting an image of a light pattern formed by light reflected from the specimen illuminated by the polarized light; and
    processing the image of the light pattern detected at the detecting step and extracting defects on the specimen by comparing the detected image with a reference image to produce a difference image and distinguishing the defects from differences caused by minute unevenness of a surface of the specimen;
    wherein in the detecting step, a polarization state of the light pattern formed by the reflected light is controlled, so as to increase modulation of the light pattern and enable detection of a maximum number of the defects by reducing a 0-th order light component reflected from the specimen.

2. The inspection method according to claim 1, wherein the detected image of the light pattern is formed by the reflected light from one chip and the reference image is an image of an adjacent chip.

3. The inspection method according to claim 1, wherein the polarization state of the light pattern is so controlled that a defect detection sensitivity is uniform in an entire chip region.

4. The inspection method according to claim 1, where the step of processing includes converting the detected image of the light pattern into an electrical signal indicative thereof.

5. An inspection method, comprising the steps of:
    illuminating a polarized light onto a specimen which has plural chips in which patterns are formed in each chip;
    detecting an image of a light pattern formed by light reflected from the specimen illuminated by the polarized light; and
    processing the image of the light pattern detected at the detecting step and extracting detects on the specimen by comparing the detected image with a reference image;
    wherein in the detecting step, a polarization state of the light pattern formed by the reflected light is controlled so as to increase modulation of the light pattern and enable detection of a maximum number of true defects by reducing a 0-th order light component reflected from the specimen.

6. The inspection method according to claim 5, where the step of processing includes converting the detected image of the light pattern into an electrical signal indicative thereof.

* * * * *